US012806300B2

(12) United States Patent
Seo et al.

(10) Patent No.: US 12,806,300 B2

(45) Date of Patent: Nov. 24, 2026

(54) PET CARE ROBOT STATION

(71) Applicant: Samsung Electronics Co., Ltd., Suwon-si (KR)

(72) Inventors: Wonyoung Seo, Suwon-si (KR); Hyunki Bae, Suwon-si (KR); Donghyun Chun, Suwon-si (KR); Hongseok Choi, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 416 days.

(21) Appl. No.: 18/131,485

(22) Filed: Apr. 6, 2023

(65) Prior Publication Data

US 2023/0241269 A1 Aug. 3, 2023

Related U.S. Application Data

(63) Continuation of application No. PCT/KR2021/011649, filed on Aug. 31, 2021.

(30) Foreign Application Priority Data

Oct. 6, 2020 (KR) ........................ 10-2020-0128551

(51) Int. Cl.

*A61L 2/10* (2026.01)
*A01K 5/02* (2006.01)

(Continued)

(52) U.S. Cl.

CPC .................. *A61L 2/10* (2013.01); *A61L 2/24* (2013.01); *A61L 2/26* (2013.01); *B08B 3/02* (2013.01);

(Continued)

(58) Field of Classification Search

CPC ..... A61L 2/10; A61L 2/24; A61L 2/26; A61L 2202/11; A61L 2202/15; A61L 2202/17; B08B 3/02; B08B 13/00; A01K 5/02

See application file for complete search history.

(56) References Cited

U.S. PATENT DOCUMENTS 5,135,721 A * 8/1992 Richard .................... A61L 2/24
425/269
5,440,216 A * 8/1995 Kim ...................... A47L 9/2894
15/340.1

(Continued)

FOREIGN PATENT DOCUMENTS

CN 105904466 A 8/2016
CN 109513023 A 3/2019

(Continued)

OTHER PUBLICATIONS

International Search Report and Written Opinion of the International Searching Authority dated Dec. 20, 2021, in connection with International Application No. PCTKR2021011649, 10 pages.

(Continued)

*Primary Examiner* — Wyatt A Stoffa

(57) ABSTRACT

Disclosed is a pet care robot station including: a housing including an entrance allowing a pet care robot to enter and exit, and an accommodating space to accommodate the pet care robot; a door provided in the housing to open and close the entrance; and a sterilizer provided in the accommodating space to remove foreign materials from an outer surface of the pet care robot.

16 Claims, 20 Drawing Sheets

(51) Int. Cl.
*A61L 2/24* (2006.01)
*A61L 2/26* (2006.01)
*B08B 3/02* (2006.01)
*B08B 13/00* (2006.01)

(52) U.S. Cl.
CPC ................ *B08B 13/00* (2013.01); *A01K 5/02* (2013.01); *A61L 2202/11* (2013.01); *A61L 2202/15* (2013.01); *A61L 2202/17* (2013.01)

(56) References Cited

U.S. PATENT DOCUMENTS

| | | | | |
|---|---|---|---|---|
| 7,791,044 | B1 * | 9/2010 | Taylor | A61L 2/10 250/493.1 |
| 8,123,871 | B2 * | 2/2012 | Brieussel | A61L 2/18 134/115 R |
| 8,381,746 | B2 * | 2/2013 | Yoon | A61L 2/22 134/123 |
| 8,591,664 | B2 * | 11/2013 | Rebstock | B08B 3/02 414/754 |
| 9,045,358 | B2 * | 6/2015 | Greuel | C02F 1/325 |
| 9,295,741 | B2 * | 3/2016 | Yerby | A61L 2/24 |
| 11,033,643 | B2 * | 6/2021 | Starkweather | A61L 2/10 |
| 11,090,399 | B2 * | 8/2021 | Starkweather | A61L 2/10 |
| 11,565,010 | B2 * | 1/2023 | Ibrahim | A47F 10/04 |
| 12,186,439 | B2 * | 1/2025 | Trapani | A61L 2/10 |
| 2006/0251540 | A1 * | 11/2006 | Benning | A61L 2/07 422/26 |
| 2007/0125306 | A1 | 6/2007 | Beecher | |
| 2007/0292324 | A1 * | 12/2007 | Jonsson | A61L 2/26 422/292 |
| 2008/0178412 | A1 * | 7/2008 | Kiter | A61L 2/10 15/4 |
| 2008/0209665 | A1 | 9/2008 | Mangiardi | |
| 2011/0079732 | A1 * | 4/2011 | Kreitenberg | A61L 2/10 250/455.11 |
| 2011/0247566 | A1 | 10/2011 | Mainini | |
| 2014/0158910 | A1 * | 6/2014 | Fletcher | A61L 2/10 250/455.11 |
| 2015/0137762 | A1 | 5/2015 | Kim et al. | |
| 2019/0262483 | A1 * | 8/2019 | Goidenko | A61L 2/10 |
| 2020/0093092 | A1 | 3/2020 | Soug | |
| 2020/0254122 | A1 * | 8/2020 | Starkweather | A61L 2/10 |
| 2021/0299311 | A1 * | 9/2021 | Yu | A01M 13/00 |
| 2021/0346552 | A1 * | 11/2021 | Eastep | A61L 2/208 |
| 2021/0362690 | A1 * | 11/2021 | Middleton | B60S 3/04 |
| 2021/0369015 | A1 * | 12/2021 | Nevitt | A61L 2/10 |
| 2022/0062477 | A1 * | 3/2022 | Hunt | A61L 2/10 |
| 2022/0194329 | A1 * | 6/2022 | Krull | B08B 3/022 |
| 2022/0305152 | A1 * | 9/2022 | Hall | A61L 2/04 |
| 2023/0042650 | A1 * | 2/2023 | Ross | A61L 2/10 |
| 2024/0197140 | A1 * | 6/2024 | Sperry | A47L 15/0065 |
| 2024/0342328 | A1 * | 10/2024 | Gillespie | A61L 2/10 |
| 2026/0151524 | A1 * | 6/2026 | Bonutti | A61L 2/10 |

FOREIGN PATENT DOCUMENTS

| | | | |
|---|---|---|---|
| CN | 111007786 | A | 4/2020 |
| JP | 2016202184 | A | 12/2016 |
| KR | 10-2007-0012109 | A | 1/2007 |
| KR | 10-2009-0066521 | A | 6/2009 |
| KR | 10-2011-0082202 | A | 7/2011 |
| KR | 10-2015-0056449 | A | 5/2015 |
| KR | 10-2017-0010131 | A | 1/2017 |
| KR | 10-2017-0015583 | A | 2/2017 |
| KR | 10-1721386 | B1 | 3/2017 |
| KR | 10-1898661 | B1 | 9/2018 |
| KR | 10-2018-0122216 | A | 11/2018 |
| KR | 10-2019-0007889 | A | 1/2019 |
| KR | 10-2019-0065610 | A | 6/2019 |
| KR | 10-2020-0116185 | A | 10/2020 |

OTHER PUBLICATIONS

Office Action dated Jul. 24, 2025, in connection with Korean Application No. 10-2020-0128551, 12 pages.

* cited by examiner

PET CARE ROBOT STATION

CROSS-REFERENCE TO RELATED APPLICATIONS

This application is a Bypass Continuation of International Application No. PCT/KR2021/011649, filed Aug. 31, 2021, which claims priority to Korean Patent Application No. 10-2020-0128551, filed Oct. 6, 2020, the disclosures of which is incorporated by reference herein in their entirety.

BACKGROUND

1. Field

The disclosure relates to a pet care robot station.

2. Description of Related Art

With a recent trend of rapidly increasing families having pets, a pet care robot playing with or feeding the pets has been developed.

The pet care robot comes into contact with a pet frequently, and at this time gets foreign materials, for example, saliva, bacteria, viruses, etc. on an outer surface thereof due to the bites or licks of the pet.

Further, the pet care robot gets dust, germs, viruses, etc. on an outer frame thereof while driving on an indoor floor, and in this state comes into contact with a user or pet, thereby adversely affecting the health of the user or pet.

SUMMARY

The disclosure is to provide a pet care robot station which keeps a pet care robot clean to take care of the hygiene of a user or pet.

According to an embodiment of the disclosure, there is provided a pet care robot station. The pet care robot station includes a housing including an entrance allowing a pet care robot to enter and exit, and an accommodating space to accommodate the pet care robot; a door provided in the housing to open and close the entrance; and a sterilizer provided in the accommodating space to remove foreign materials from an outer surface of the pet care robot.

The pet sterilizer may include an ultraviolet (UV) lamp to emit UV light.

The pet accommodating space may include a reflective material on an inner wall thereof to reflect the UV light.

The door may include a reflective material on a surface thereof facing the inside of the accommodating space to reflect the UV light.

The door may include: a blocking plate larger than the entrance; and a pair of supporters provided at opposite sides of the blocking plate and rotatably supported on opposite lateral walls of the entrance.

The door may include a motor to rotate the pair of supporters.

The pet care robot station may further include a charger provided in the accommodating space to charge the pet care robot.

The pet care robot station may further include a sensor configured to detect a location of the pet care robot; and a processor configured to guide the pet care robot from the detected location to be located in the charger (e.g., in contact with the charger).

The housing may include a wheel guide on a bottom thereof to guide the pet care robot to the charger.

The pet care robot station may further include: a camera configured to detect foreign materials on an outer portion of the pet care robot; and a processor configured to call the pet care robot to the accommodating space based on the foreign materials detected on the outer portion of the pet care robot.

The sterilizer may include a cleaning nozzle to spray a cleanser onto a surface of the pet care robot.

The pet accommodating space may include a cleaning space to clean the pet care robot, and a sterilizing space partitioned from the cleaning space to sterilize the pet care robot.

The cleaning space may include a font entrance allowing the pet care robot to come in and out, a robot through hole may be provided between the cleaning space and the sterilizing space and allowing the pet care robot to pass therethrough, and the door may be selectively rotated between a first position for blocking the front entrance and a second position for blocking the robot through hole.

According to the disclosure, a pet care robot station removes foreign materials, for example, saliva, germs, viruses, dust, contaminants, etc. smeared on an outer surface of a pet care robot when the pet care robot is being charged or when the foreign materials are detected, thereby taking care of the heath of a user or pet.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 20, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Below, embodiments of a pet care robot station 2 will be described in detail with reference to the accompanying drawings. In the following descriptions, details about publicly known functions or features that cloud the gist of the disclosure will be omitted from the disclosure.

Figure 1:
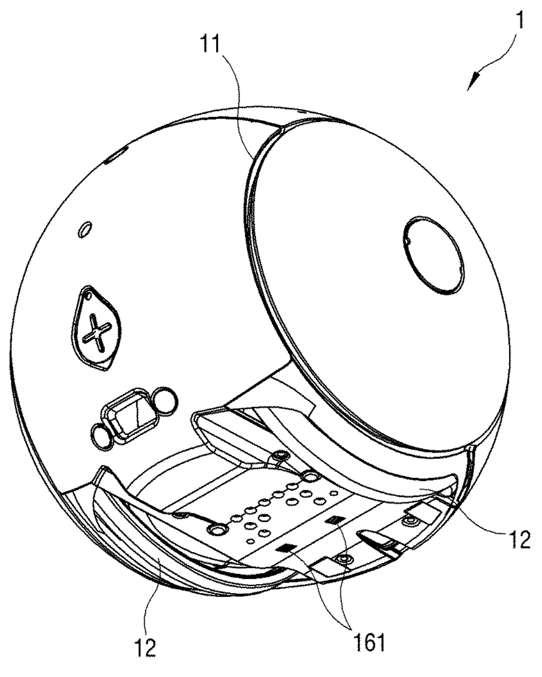
FIG. 1 illustrates a pet care robot.
Figure 2:
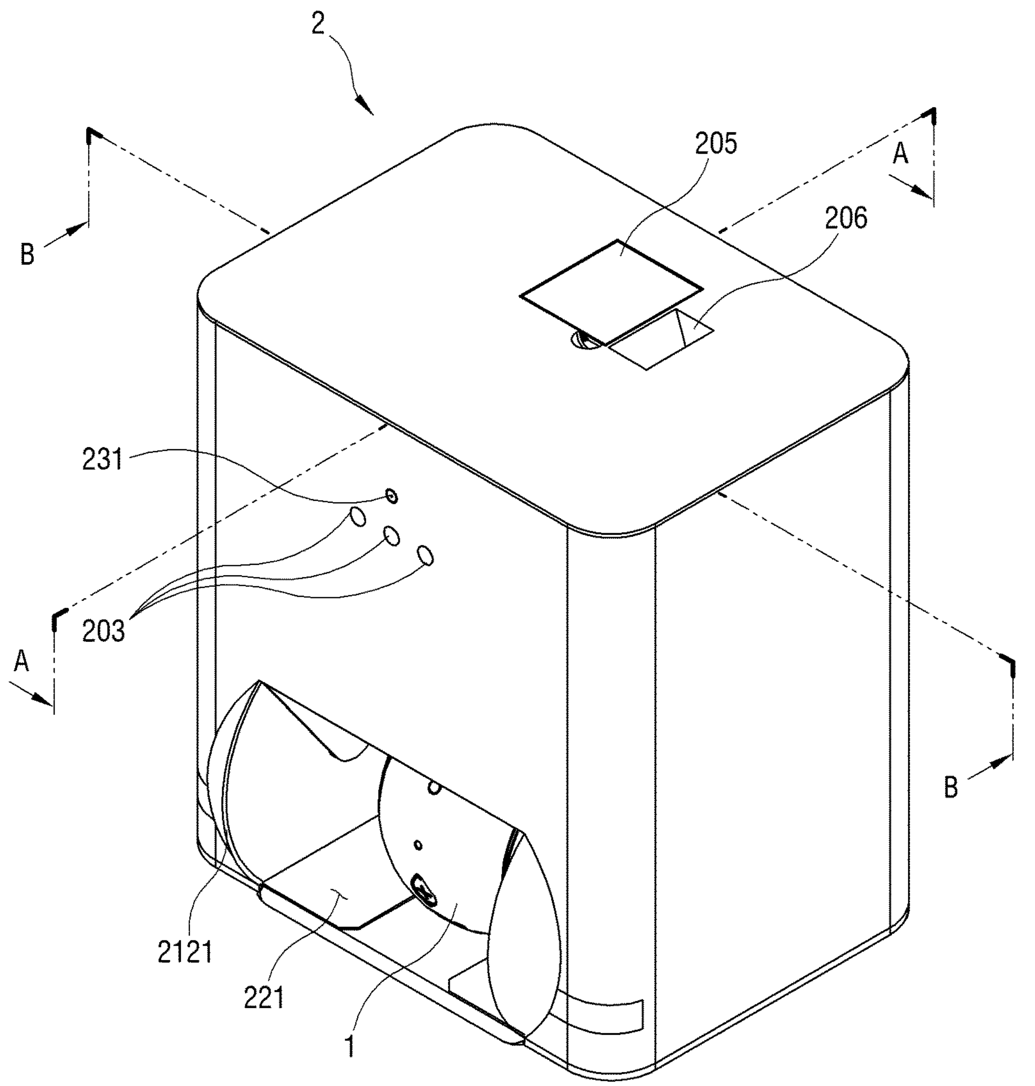
FIG. 2 illustrates the whole of a pet care robot station according to a first embodiment of the disclosure.

FIG. 1 illustrates a pet care robot 1, and FIG. 2 illustrates the whole of a pet care robot station 2 according to a first embodiment of the disclosure.

As shown in FIG. 1, the pet care robot 1 includes a main body 11 and two wheels 12.

Figure 11:
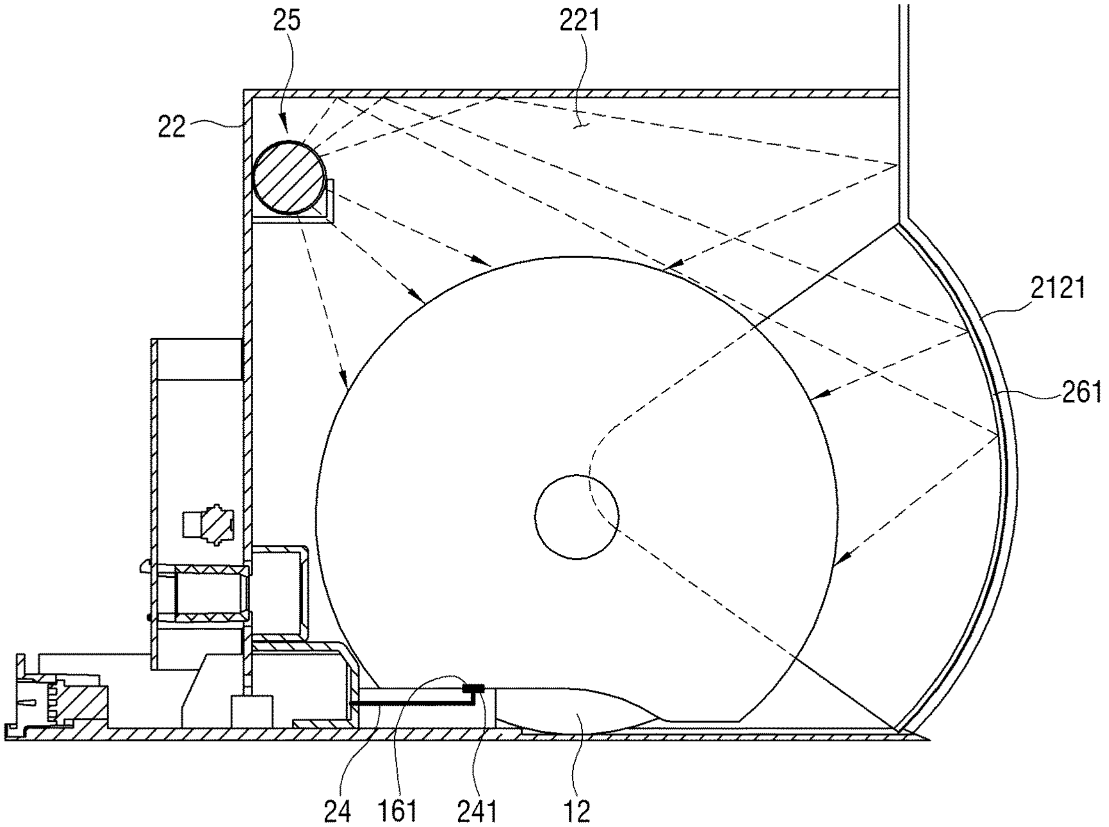
FIG. 11 illustrates that a pet care robot is accommodated in an inner housing and a door is closed.

The main body 11 is provided with battery terminals 161 in a lower portion thereof to charge a battery 16 (see FIG. 11).

The pet care robot 1 travels as the two wheels 12 rotate. The pet care robot 1 autonomously travels by identifying a path to move by itself through a first sensor 14 (see FIG. 11).

Referring to FIG. 2, the pet care robot station 2 includes an entrance 2121 through which the pet care robot 1 can enter and exit, and an accommodating space 221 in which the pet care robot 1 can be accommodated. The entrance 2121 protrudes, having arch shapes at the opposite sides thereof, to secure a space in which a door 261 (see FIG. 8) (to be described later) is allowed to rotate.

The pet care robot station 2 is, for example, provided with three light emitting diodes (LED) 203 and a camera 231 in the front thereof.

The three LEDs 203 indicate the states of the pet care robot station 2 where the pet care robot 1 is, for example, being out, charged, sterilized, etc.

The pet care robot station 2 is provided with a treat storage 205 and a treat outlet 206 on the top thereof.

The treat storage 205 is filled with treats that a pet likes.

The treat outlet 206 discharges the treats filled in the treat storage 205 to the outside. The discharged treats are provided to a pet following the pet care robot 1 in time for feeding. The treats are discharged through the treat outlet 206 at an angle of, for example, 45 degrees to be thrown far away from the pet care robot station 2.

Figure 3:
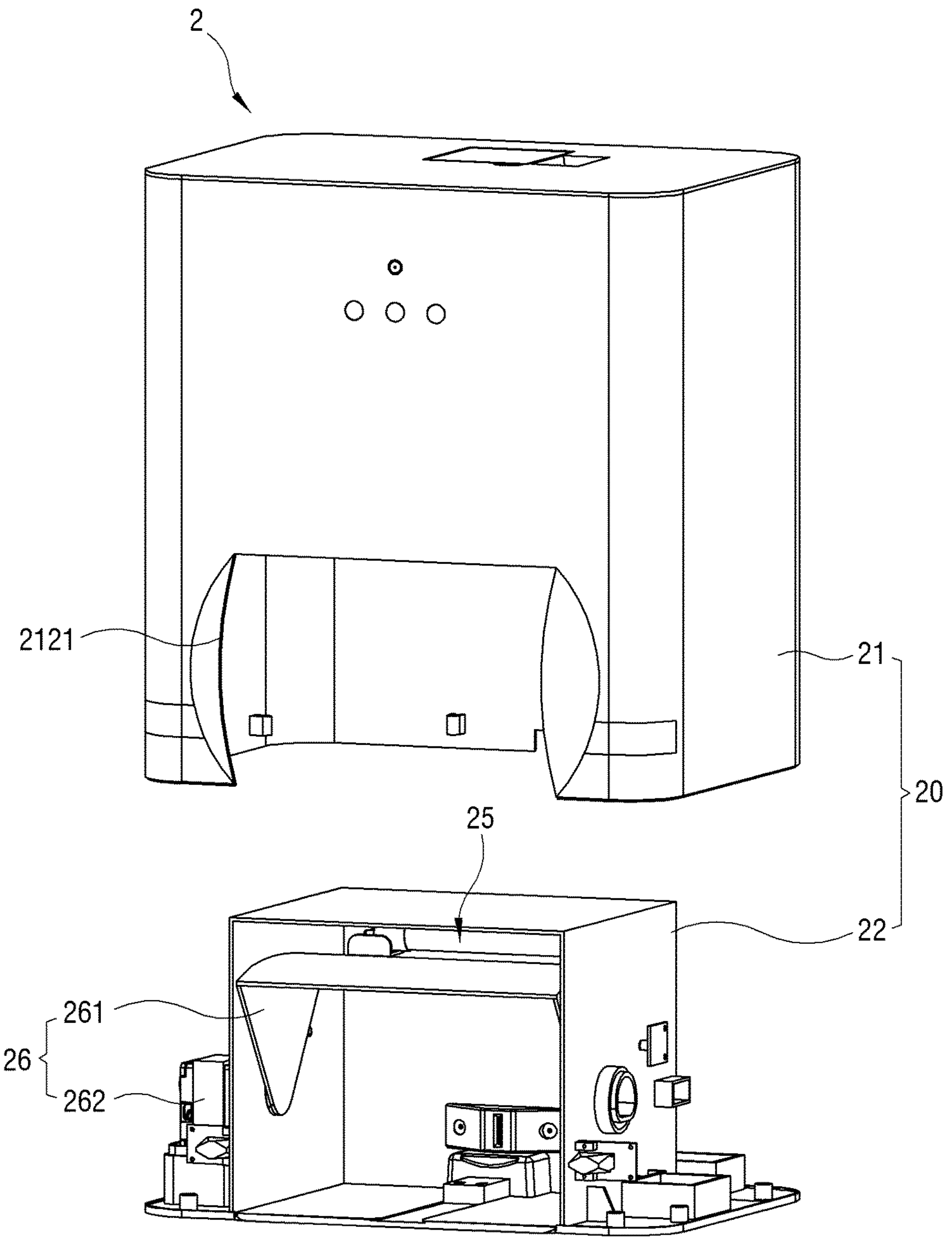
FIG. 3 illustrates an exploded view of a pet care robot station.
Figure 4:
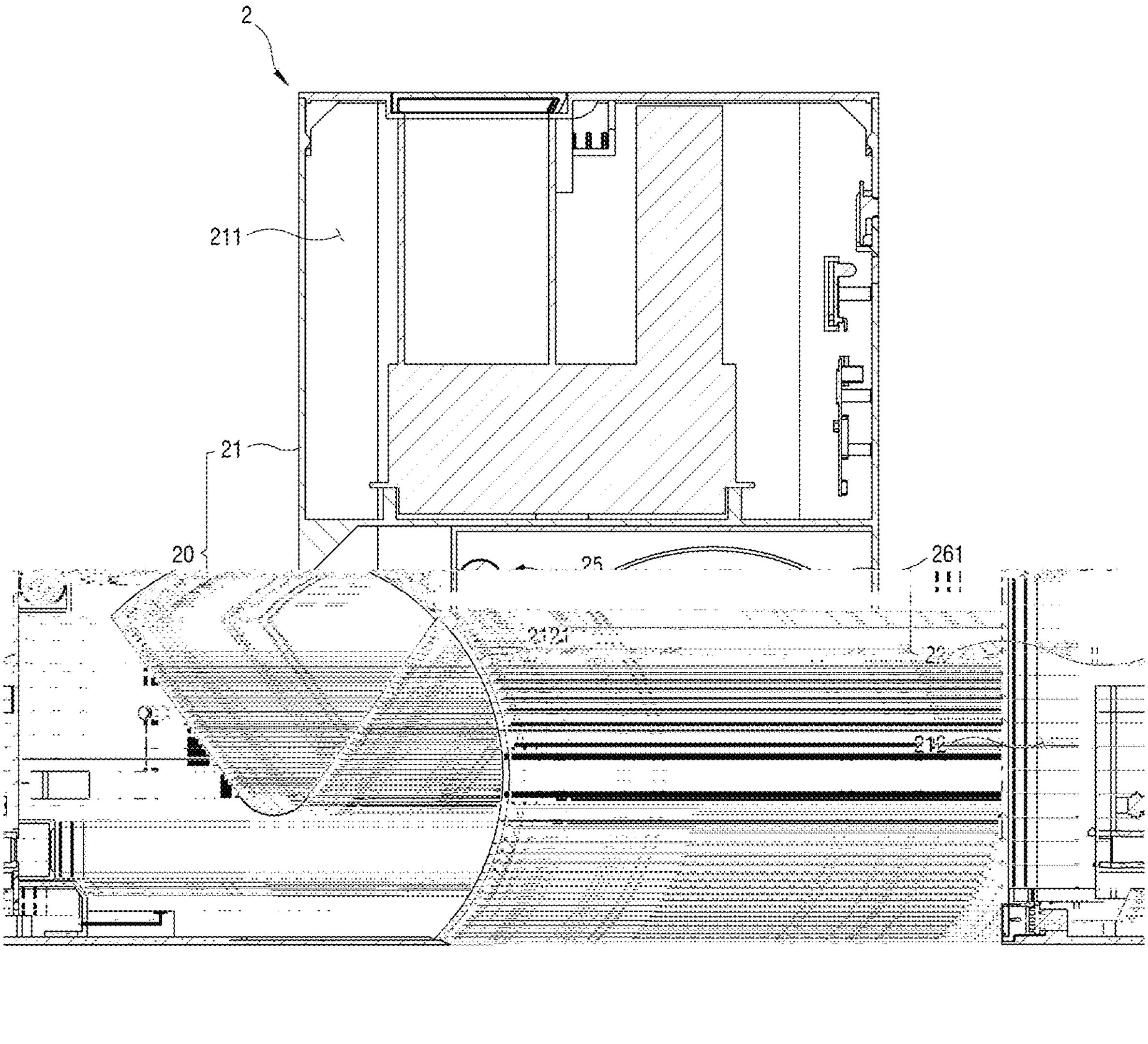
FIG. 4 illustrates a view showing a cross-section taken along line A-A of FIG. 2.
Figure 5:
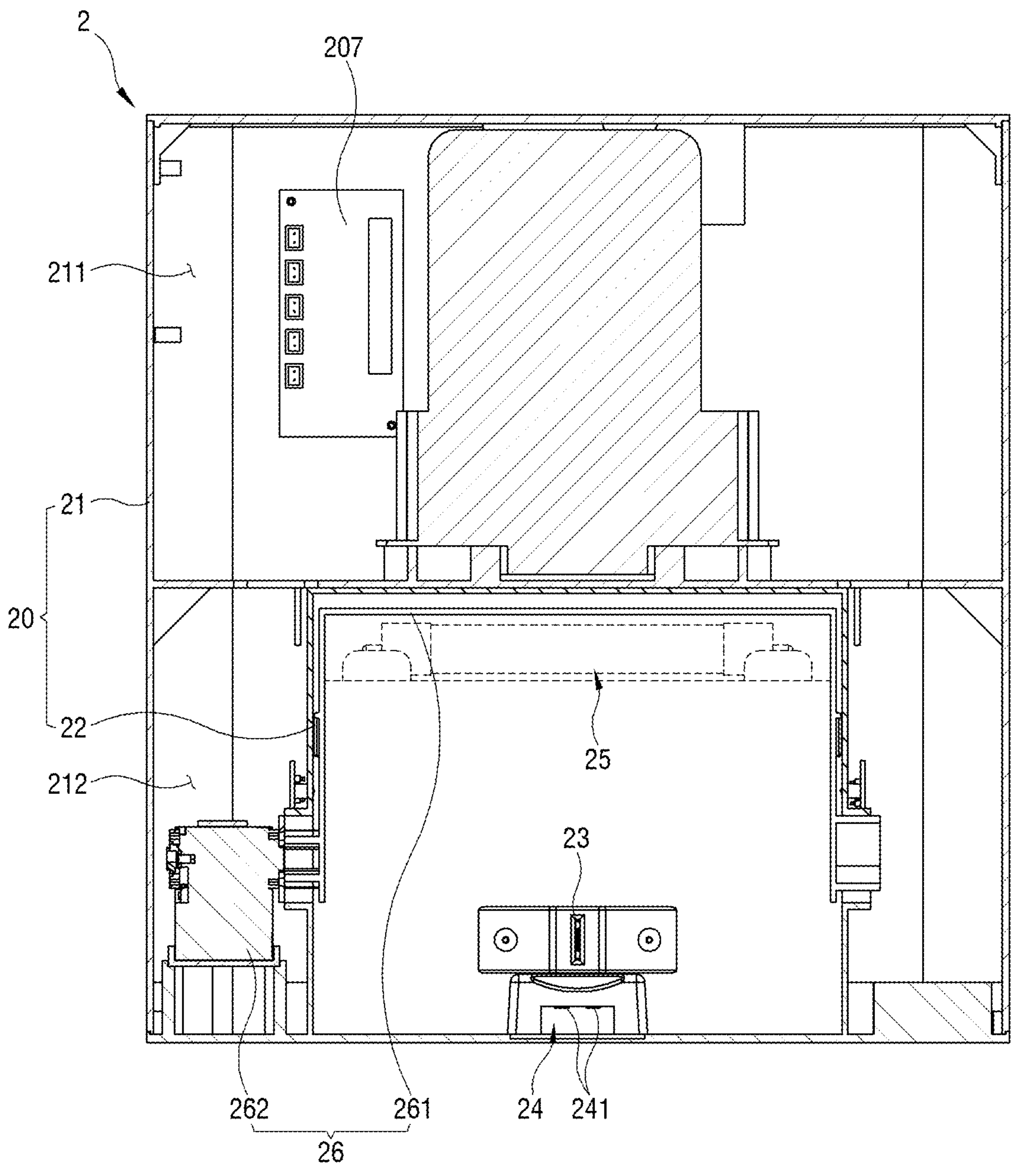
FIG. 5 illustrates a view showing a cross-section taken along line B-B of FIG. 2.

FIG. 3 illustrates an exploded view of the pet care robot station 2, FIG. 4 illustrates a view showing a cross-section taken along line A-A of FIG. 2, and FIG. 5 is a view showing a cross-section taken along line B-B of FIG. 2.

Referring to FIGS. 3 to 5, the pet care robot station 2 includes a housing 20.

The housing 20 includes an outer housing 21 and an inner housing 22.

The outer housing 21 includes a first space 211 provided in an upper portion thereof, and a second space 212 partitioned from the first space 211 and provided in a lower portion thereof.

The first space 211 is provided with an electronic board 207 having an electronic circuit and electronic parts to operate the pet care robot station 2.

The second space 212 includes the entrance 2121 communicating with the inner housing 22 accommodated therein. The size of the entrance 2121 is large enough to allow the pet care robot 1 to enter and exit.

The second space 212 accommodates the inner housing 22 in the middle thereof. The inner housing 22 is installed to be opened toward the entrance 2121 of the outer housing 21.

The housing 20 is not limited to the structure of the outer housing 21 and the inner housing 22, and may be a single structure.

Below, embodiments shown in FIG. 3 will be described in detail with reference to FIGS. 6 to 11.

Figure 6:
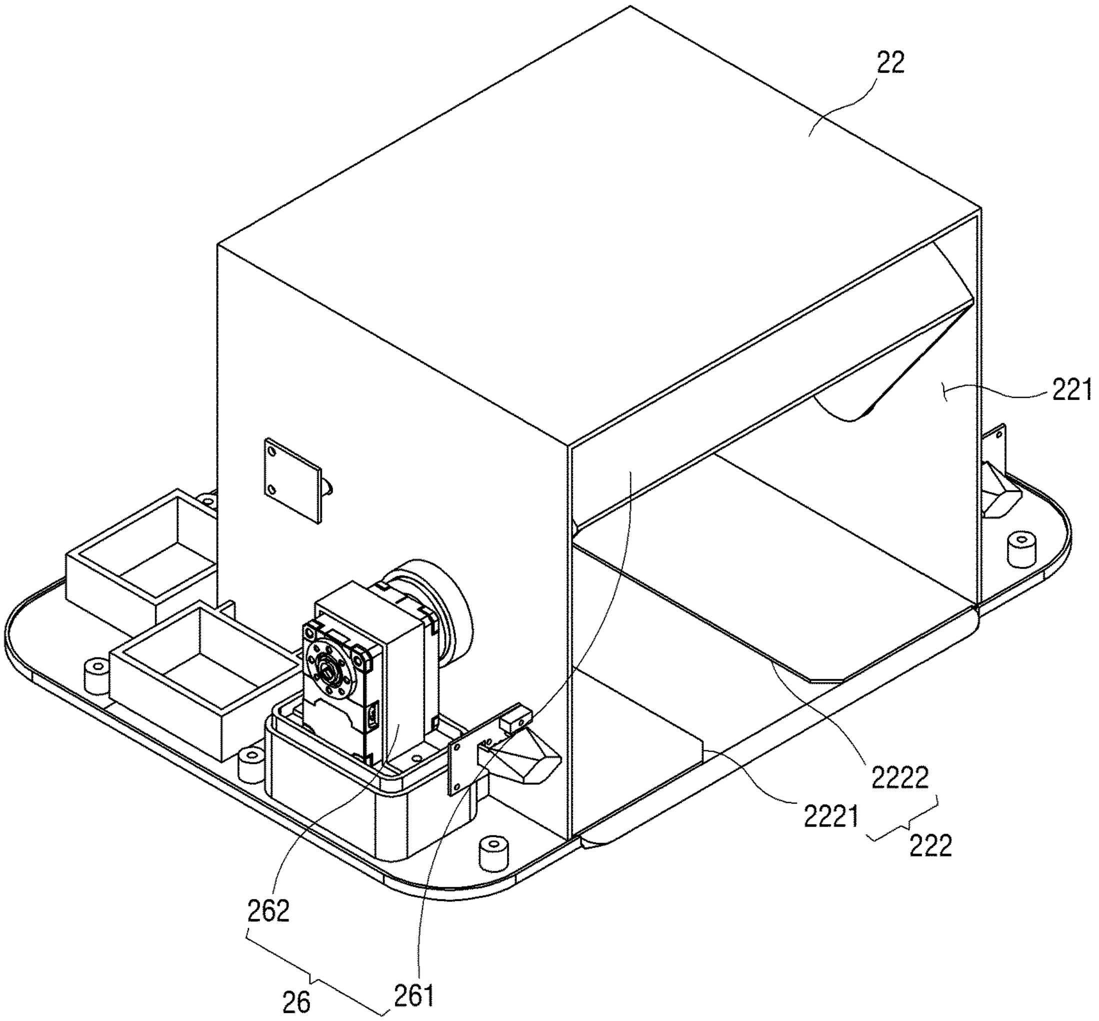
FIG. 6 illustrates the whole of an inner housing.
Figure 7:
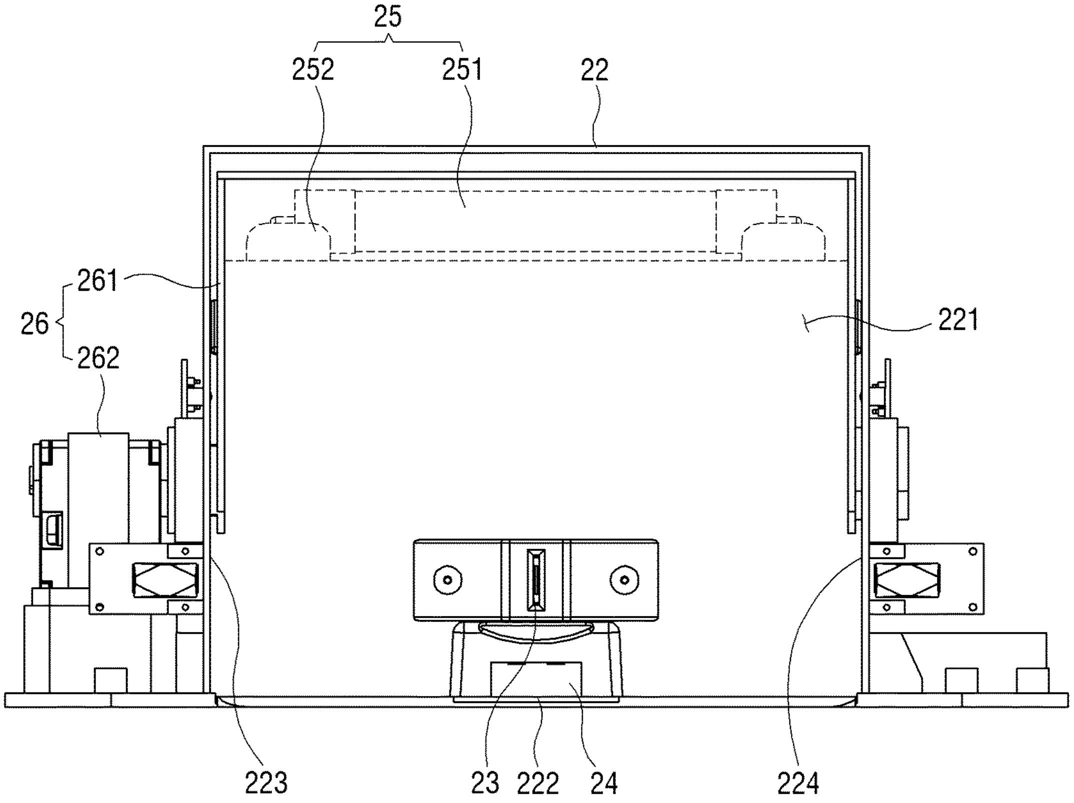
FIG. 7 illustrates the front of an inner housing.
Figure 8:
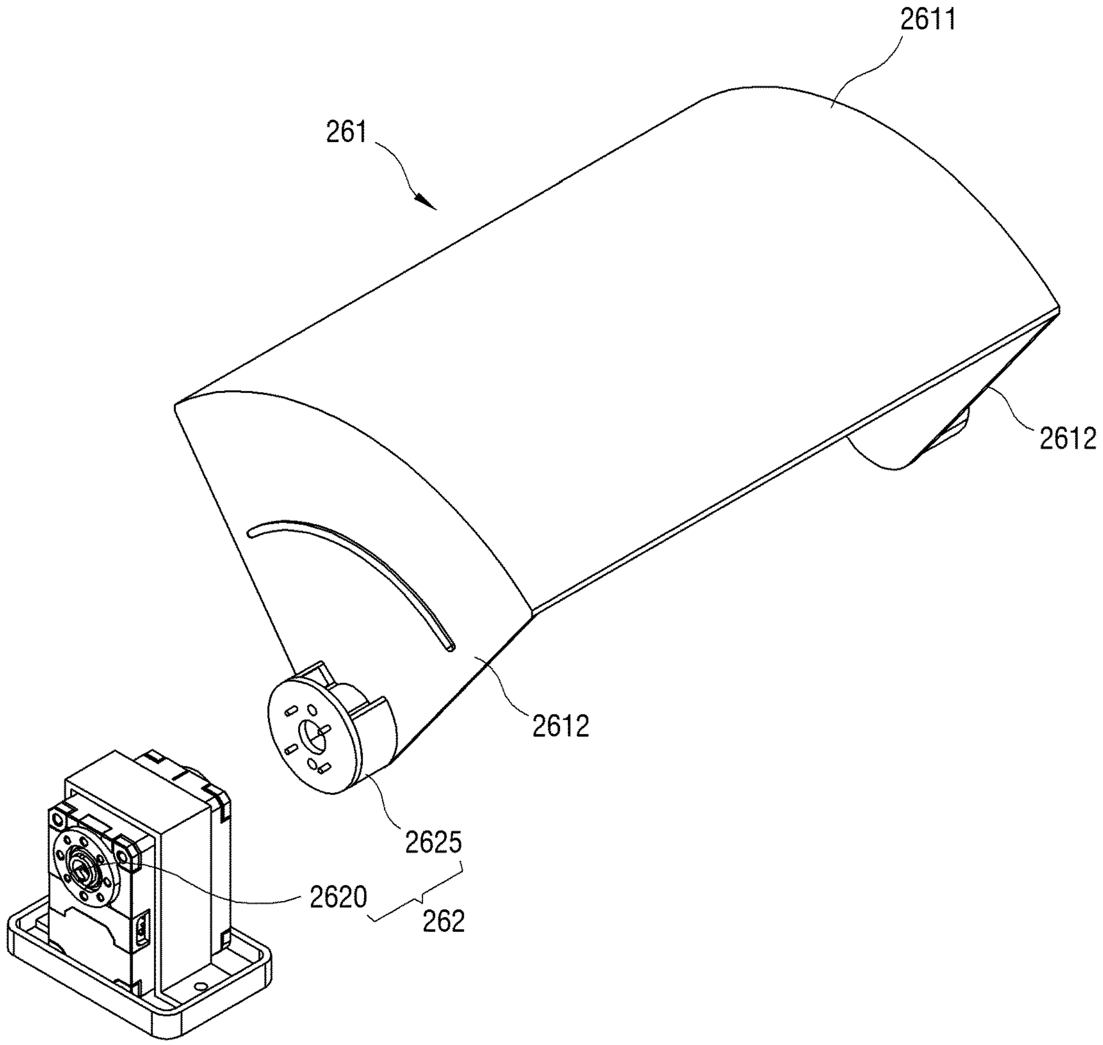
FIG. 8 illustrates a door assembly.
Figure 9:
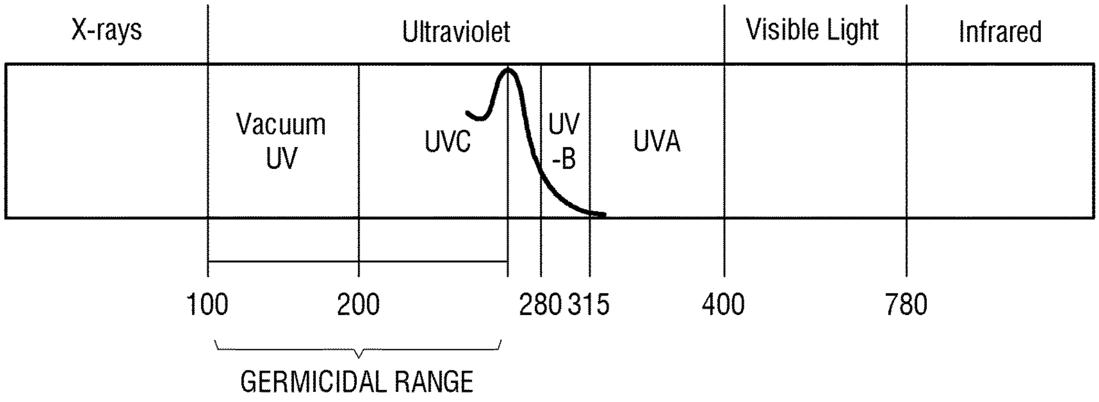
FIG. 9 illustrates the spectrum of light.
Figure 10:
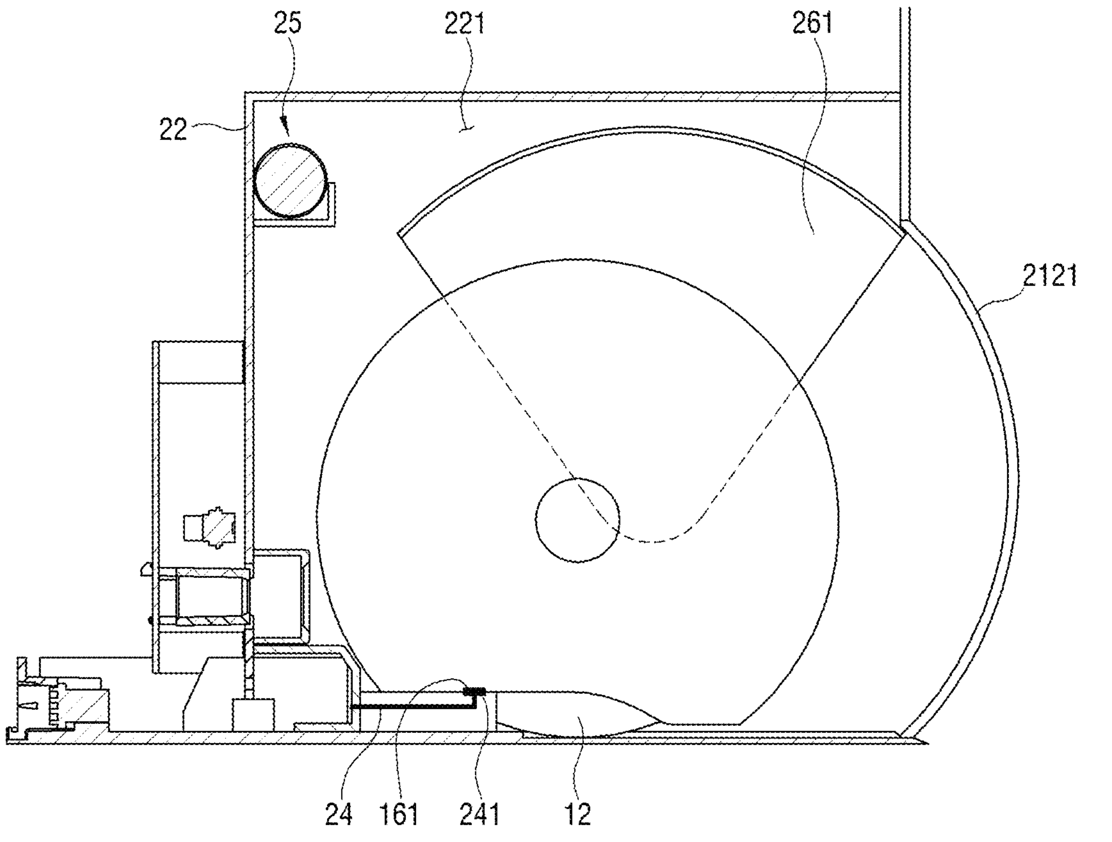
FIG. 10 illustrates that a pet care robot is accommodated in an inner housing and a door is open.

FIG. 6 illustrates the whole of the inner housing 22, FIG. 7 illustrates the front of the inner housing 22, FIG. 8 illustrates a door assembly 26, FIG. 9 illustrates the spectrum of light, FIG. 10 illustrates that the pet care robot 1 is accommodated in the inner housing 22 and the door 261 is open, and FIG. 11 illustrates that the pet care robot 1 is accommodated in the inner housing 22 and the door 261 is closed.

Referring to FIGS. 6 and 7, the pet care robot station 2 includes a second sensor 23, a charger 24, a sterilizer 25, and the door assembly 26, which are provided in the inner housing 22.

The inner housing 22 is shaped like a box of, e.g., a hexahedron, opened frontwards. The inner housing 22 includes the accommodating space 221 to accommodate the pet care robot 1 therein. The inner housing 22 includes at least one wall in shaped like a box forming the accommodating space.

The inner housing 22 is provided with a wheel guide 222 on the bottom thereof to guide the pet care robot 1 toward charging terminals 241 (see FIG. 5 or 9). The wheel guide 222 may be implemented by a guide groove 2222 that receives the wheels 12 of the pet care robot 1 and extended from an entryway 2221 at the side of the entrance 2121 to the charging terminals 241. The entryway 2221 may be formed to be sufficiently wider than a distance between the two wheels 12 of the pet care robot 1 so that the two wheels 12 can be easily accommodated therein, and may be gradually connected to the guide groove 2222. The guide groove 2222 may be formed to have a width corresponding to the distance between the two wheels 12 of the pet care robot 1. The wheel guide 222 may be formed as a single groove to accommodate all the two wheels 12, or as a pair of grooves to respectively guide the two wheels 12.

The pet care robot 1 moves to the entrance 2121 of the pet care robot station 2 in response to a command from the pet care robot station 2 or according to the pet care robot's own traveling program. The pet care robot 1 goes forward along the guide groove 2222 while the two wheels 12 enter the entryway 2221 of the wheel guide 222, and therefore the battery terminals 161 (see FIG. 1) can be accurately placed on the charging terminals 241.

The pet care robot 1 may be guided along the wheel guide 222, and thus the battery terminals 161 (see FIG. 1) of the main body 11 may come into contact into the charging terminals 241 of the charger 24.

The inner wall of the accommodating space 221 may include a reflective material capable of reflecting ultraviolet (UV) light emitted from a UV lamp 251 (to be described later). The reflective material may contain paint from which light is reflected. The reflective material may be made of white plaster of aluminum, the surface of which has reflectivity. The reflective material may include polished stainless steel.

The second sensor 23 may be implemented by a camera, an infrared (IR) sensor, a radar, an ultrasonic sensor, etc. to detect the pet care robot 1, a pet, people, etc. around the pet care robot station 2.

The second sensor 23 may detect the location of the pet care robot 1, the presence/absence of foreign materials on the outer surface of the pet care robot 1, the motion states of the pet care robot 1, etc.

The second sensor 23 may detect whether the pet care robot 1 is playing with a pet, whether the pet is coming to the pet care robot station 2 while following the pet care robot 1, etc.

The second sensor 23 may be used to guide the pet care robot 1 to approach the charging terminals 241 in the accommodating space 221 of the pet care robot station 2.

The charger 24 includes the charging terminals 241 exposed on the bottom of the accommodating space 221 of the inner housing 22. The charging terminals 241 are provided to protrude at points where the wheel guide 222 ends. The charging terminals 241 are positioned to be in contact with the battery terminals 161 provided on the bottom of the main body 11 when the pet care robot 1 has moved along the wheel guide 222.

The sterilizer 25 may be implemented by the UV lamp 251. Both ends of the UV lamp 251 are supported on lamp supporters 252. The UV lamp 251 may be installed in a rear upper portion of the inner housing 22 to prevent a user from being directly exposed to the UV light through the entrance 2121.

The UV lamp 251 emits the UV light in the accommodating space 221 of the inner housing 22. The UV light may be irradiated onto the pet care robot 1 accommodated in the accommodating space 221 to sterilize germs, viruses, and the like smeared on the outer surface of the pet care robot 1. The UV lamp 251 may emit the UV light while the pet care robot 1 is being charged. The UV lamp 251 may emit the UV light for a preset period of time, e.g., about 2 to 4 hours.

The UV light may, as shown in FIG. 9, have a wavelength of about 10 to 397 nanometers (nm). The UV light may be classified into UVA of 315 to 380 (nm), UVB of 280 to 315 nm UVB, UVC of 200 to 280 (nm), and vacuum UV of 100 to 200 (nm). The UV light generally used in the sterilization is the UVC of 200-280 (nm).

Referring to FIGS. 6 and 8, the door assembly 26 includes the door 261 and a door actuator 262.

The door assembly 26 blocks the entrance 2121 with the door 261 while the pet care robot 1 is accommodated in the accommodating space 221. Therefore, it is possible to prevent the UV light emitted from the UV lamp 251 from leaking to the outside. Further, closing the door 261 of the entrance 2121 may prevent a pet from becoming bored with seeing the pet care robot 1 frequently.

The door 261 includes a blocking plate 2611, and a pair of supporters 2612 bent and extended integrally at the opposite sides of the blocking plate 2611.

The blocking plate 2611 has a larger area than the entrance 2121 of the outer housing 21. Thus, when the blocking plate 2611 blocks the entrance 2121, the blocking plate 2611 overlaps the inner surface of the entrance 2121, thereby preventing the UV light from leaking.

The pair of supporters 2612 are rotatably supported at opposite walls 223 and 224 of the inner housing 22.

The door actuator 262 includes a motor 2620, and a reduction gear 2625. The reduction gear 2625 is coupled to one of the pair of supporters 2612 to rotate the door 261.

The door 261 may include a reflective material or a reflective paint applied to the surface thereof facing the accommodating space 221 to reflect the UV light emitted from the UV lamp 251.

Below, a method of controlling the pet care robot station 2 according to an embodiment of the disclosure will be described with reference to FIGS. 10 and 11.

The pet care robot station 2 may operate in a charging mode and a sterilizing mode.

In the charging mode, the pet care robot 1 that arrives at the entrance 2121 of the pet care robot station 2 for the purpose of charging may move to the location of the charging terminals 241 while finding a direction by recognizing infrared (IR) light emitted from the second sensor (e.g., an IR sensor) 23 placed inside the door 261 of the pet care robot station 2. In this case, as shown in FIG. 10, the battery terminals 161 of the pet care robot 1 may come into contact with the charging terminals 241 of the pet care robot station 2. Further, the door 261 may be in the open position in which the blocking plate 2611 faces upwards in the accommodating space 221. Of course, when both the charging mode and the sterilizing mode are performed at the same time, the door 261 of the pet care robot station 2 may as shown in FIG. 11 be in the closed position where the entrance 2121 is blocked.

In the sterilizing mode, the pet care robot station 2 may rotate the door 261 to be in the closed position so that the blocking plate 2611 can completely block the front, i.e., the entrance 2121 (e.g., opening) of the accommodating space 221. Therefore, the pet care robot station 2 may control the sterilizer 25 to emit the UV light for, for example, 2 to 4 hours to sterilize the pet care robot 1 located in the accommodating space 221.

Figure 12:
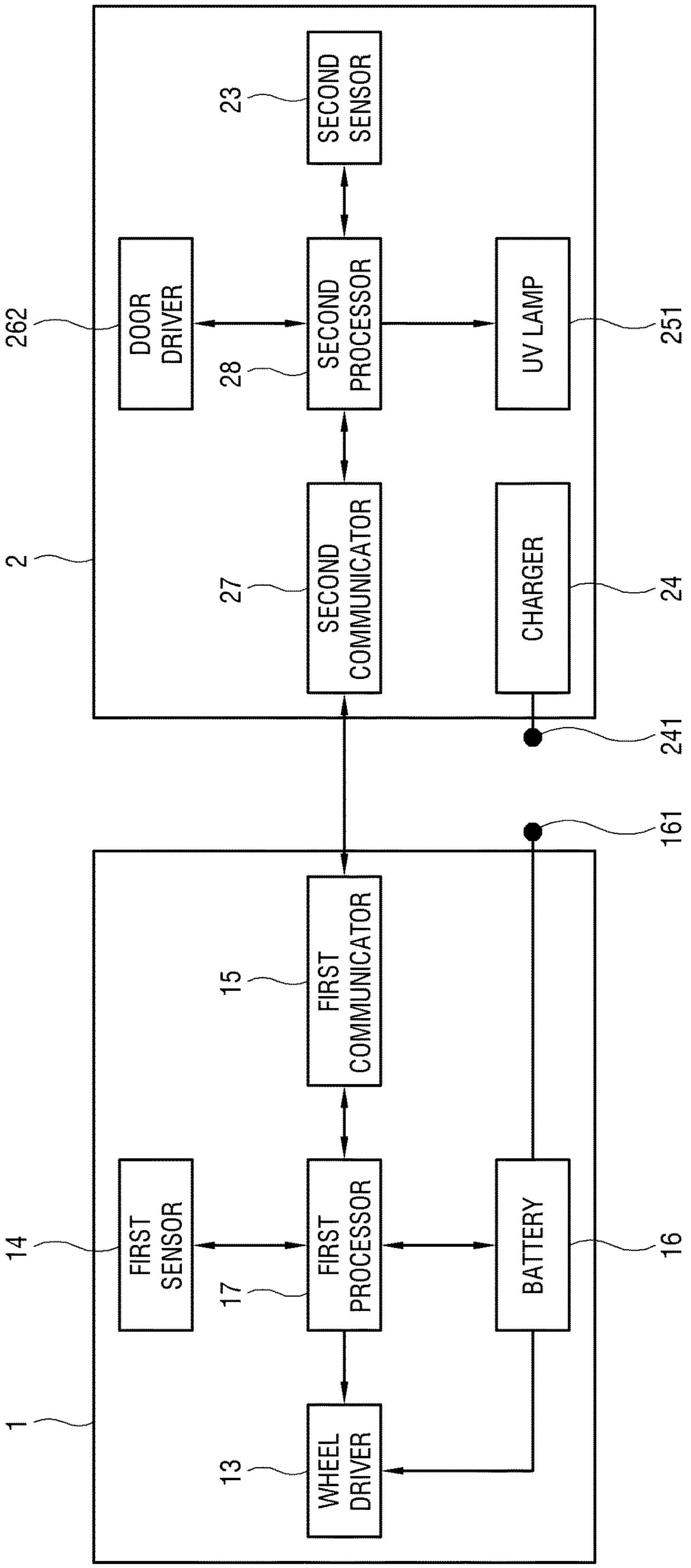
FIG. 12 illustrates a block diagram of a pet care robot and the pet care robot station according to the first embodiment of the disclosure.

FIG. 12 is a block diagram of the pet care robot 1 and the pet care robot station 2 according to an embodiment of the disclosure.

Referring to FIG. 12, the pet care robot 1 includes a wheel driver 13, the first sensor 14, a first communicator 15, the battery 16, and a first processor 17.

The wheel driver 13 rotates the wheels 12 of the pet care robot 1. The wheel driver 13 may include a wheel driving motor that generates motive power, a gear unit that transmits the motive power from the wheel driving motor to the wheels 12, and a suspension for passing an obstacle.

The first sensor 14 may detect the surroundings of the pet care robot 1, for example, obstacles, a pet, people, etc. to control a traveling direction or a playing operation. The first sensor 14 may include a camera, an IR sensor, a radar, an ultrasonic sensor, etc.

The first communicator 15 may communicate with the pet care robot station 2 or a user's mobile device or remote controller. The first communicator 15 may transmit information about the surrounding situations of the pet care robot 1 to the pet care robot station 2 or a user or may receive a control command from the pet care robot station 2 or the user.

The first communicator 15 may include connection interfaces for wireless network devices, such as Wi-fi, Bluetooth, ZigBee, Z-wave, radio frequency identification (RFID), WiGig, Wireless HD, ultra-wide band (UWB), wireless universal serial bus (USB), near field communication (NFC), etc.

The first communicator 15 may include an IR transceiver (e.g., including an IR transceiver module) to transmit and/or receive a remote-control signal.

The first communicator 15 may include connection interfaces for mobile communication devices, such as 2G to 5G.

The battery 16 may supply electric power to be used in the pet care robot 1. The battery 16 is chargeable and dischargeable, and includes the charging terminals 161 exposed to the bottom of the main body 11 as shown in FIG. 1 for the charging.

The first processor 17 generally controls the components of the pet care robot 1.

The first processor 17 controls the pet care robot 1 to travel based on the information about the situations detected by the first sensor 14. The first processor 17 may perform control for a specific sound, a specific pattern motion, a return for the charging, etc. based on a set program or a control command from a user or the pet care robot station 2.

The first processor 17 may include at least one general-purpose processor that loads at least a part of a control program from a nonvolatile memory, in which the control program is installed, into a volatile memory, and executes the loaded control program, and may be implemented as, for example, a central processing unit (CPU), an application processor (AP), a microprocessor, etc.

Referring back to FIG. 12, the pet care robot station 2 includes the second sensor 23, the charger 24, the UV lamp 251, the door actuator 262, a second communicator 27, and a second processor 28.

The second sensor 23, the charger 24, the UV lamp 251, and the door actuator 262 have been described above, and thus repetitive descriptions thereof will be avoided.

The second communicator 27 may communicate with the pet care robot 1 or a user's mobile device or remote controller. The second communicator 27 may transmit information the information about the surrounding situations to a user or receive a control command from the user. The second communicator 27 may transmit a control command to the pet care robot 1.

The second communicator 27 may include connection interfaces for wireless network devices, such as Wi-fi, Bluetooth, ZigBee, Z-wave, RFID, WiGig, Wireless HD, UWB, wireless USB, NFC, etc.

The second communicator 27 may include an IR transceiver module for transmitting and/or receiving a remote-control signal.

The second communicator 27 may include connection interfaces for mobile communication devices, such as 2G to 5G.

The second processor 28 may control the pet care robot 1 at a set time to guide a pet to the pet care robot station 2.

The second processor 28 may call the pet care robot 1 based on the second sensor 23 detecting that foreign materials are smeared on the outer surface of the pet care robot 1.

The second processor 28 may provide treats to a pet based on a user's command or a preset program.

The second processor 28 may control the door actuator 262 to make the door 261 block the entrance 2121 when the pet care robot 1 is in the charging mode.

The second processor 28 may control the door actuator 262 to make the door 261 open the entrance 2121 when the charging is completed or the operation time of the UV lamp 251 is up.

The second processor 28 may detect the conditions of the pet and transmit the detected conditions to a user's mobile device.

Figure 13:
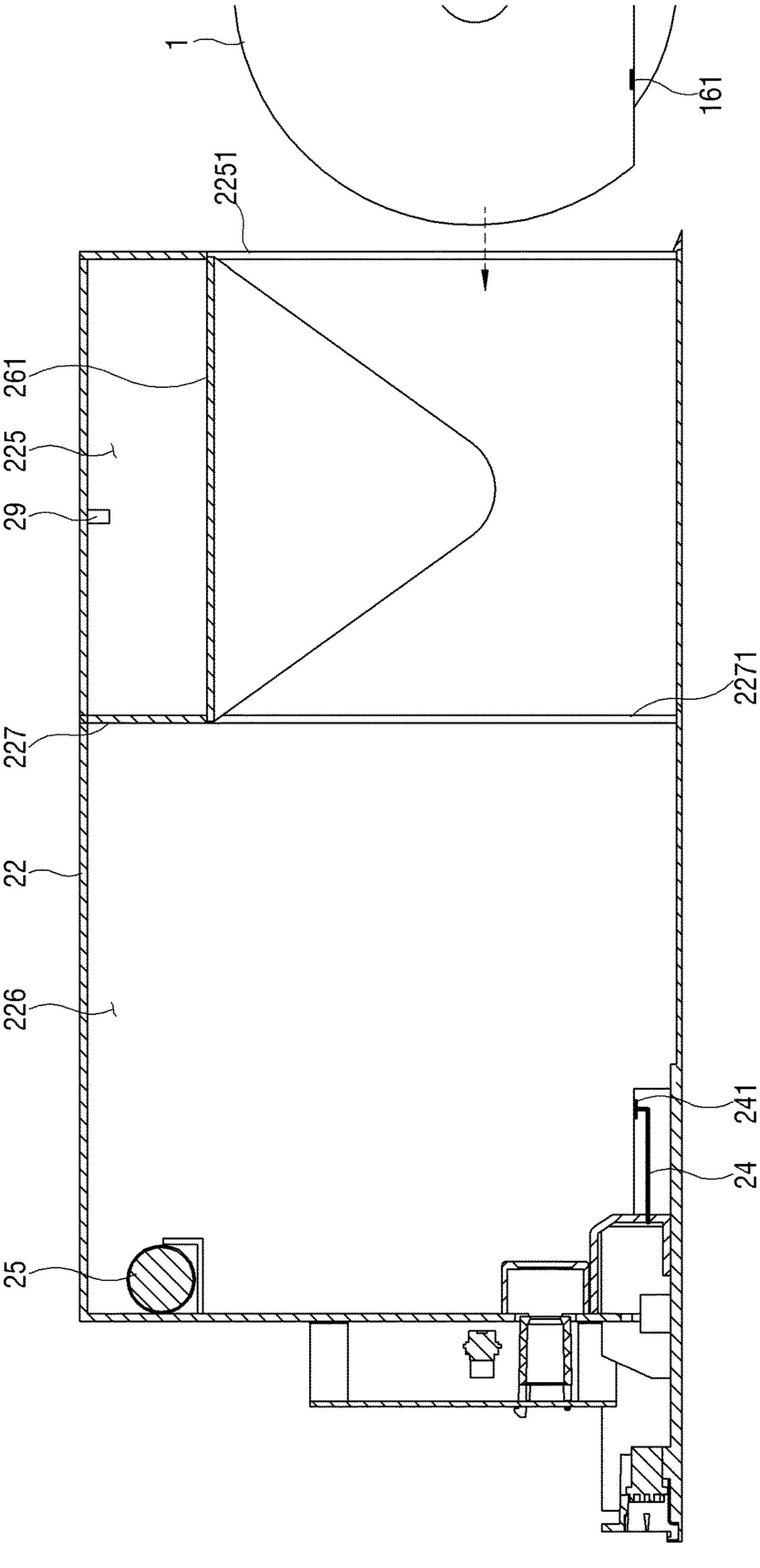
FIG. 13 illustrates a pet care robot station according to a second embodiment of the disclosure.

FIG. 13 illustrates the pet care robot station 2 according to a second embodiment of the disclosure.

Referring to FIG. 13, the pet care robot station 2 includes a cleaning unit 29 for cleaning the pet care robot 1. The cleaning unit 29 includes a cleanser tank 291, a pump 292, and a cleaning nozzle 293. The pump 292 may supply a cleanser stored in the cleanser tank 291 to the cleaning nozzle 293 provided on the ceiling of the inner housing 22 through a cleanser pipe 294.

The cleanser sprayed through the cleaning nozzle 293 cleans the pet care robot 1. The cleanser used in the cleaning may be collected in a lower cleanser collecting space 229 through a hole 2281 on the bottom 228 of the inner housing 22, and stored in the cleanser tank 291 through a discharging pipe 295.

The cleanser may employ a first-class cleanser that is harmless to a human body or pets. The cleanser may be used as being diluted with an appropriate amount of water.

A structure for preventing the cleanser from leaking to the outside when the cleaning is performed may employ the structure of the entrance 2121 of the outer housing 21 shown in FIGS. 2 to 4 and the blocking plate 2611 of the door 261 shown in FIG. 8.

Figure 14:
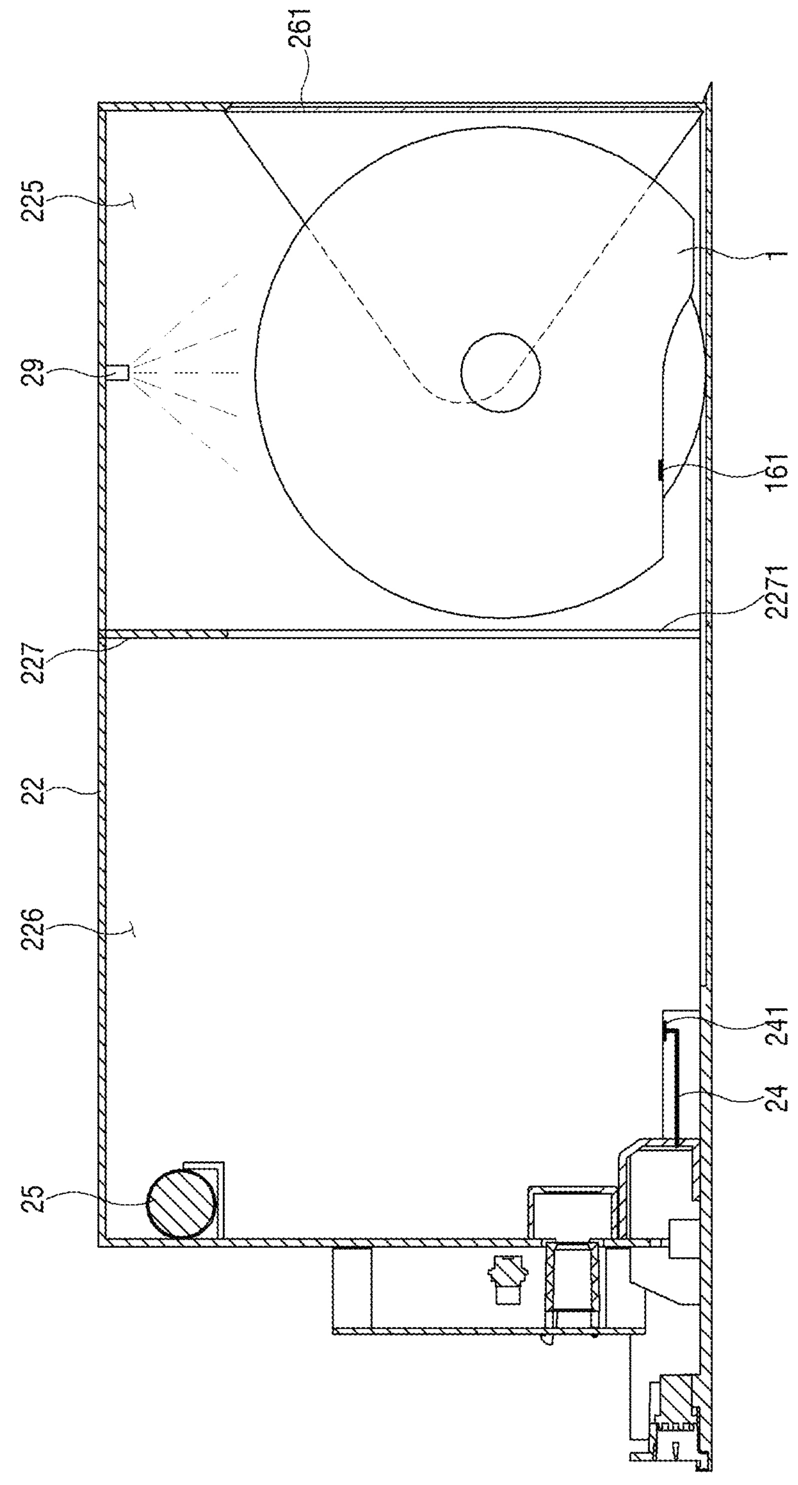
FIG. 14 illustrates a pet care robot station according to a third embodiment of the disclosure.
Figure 15:
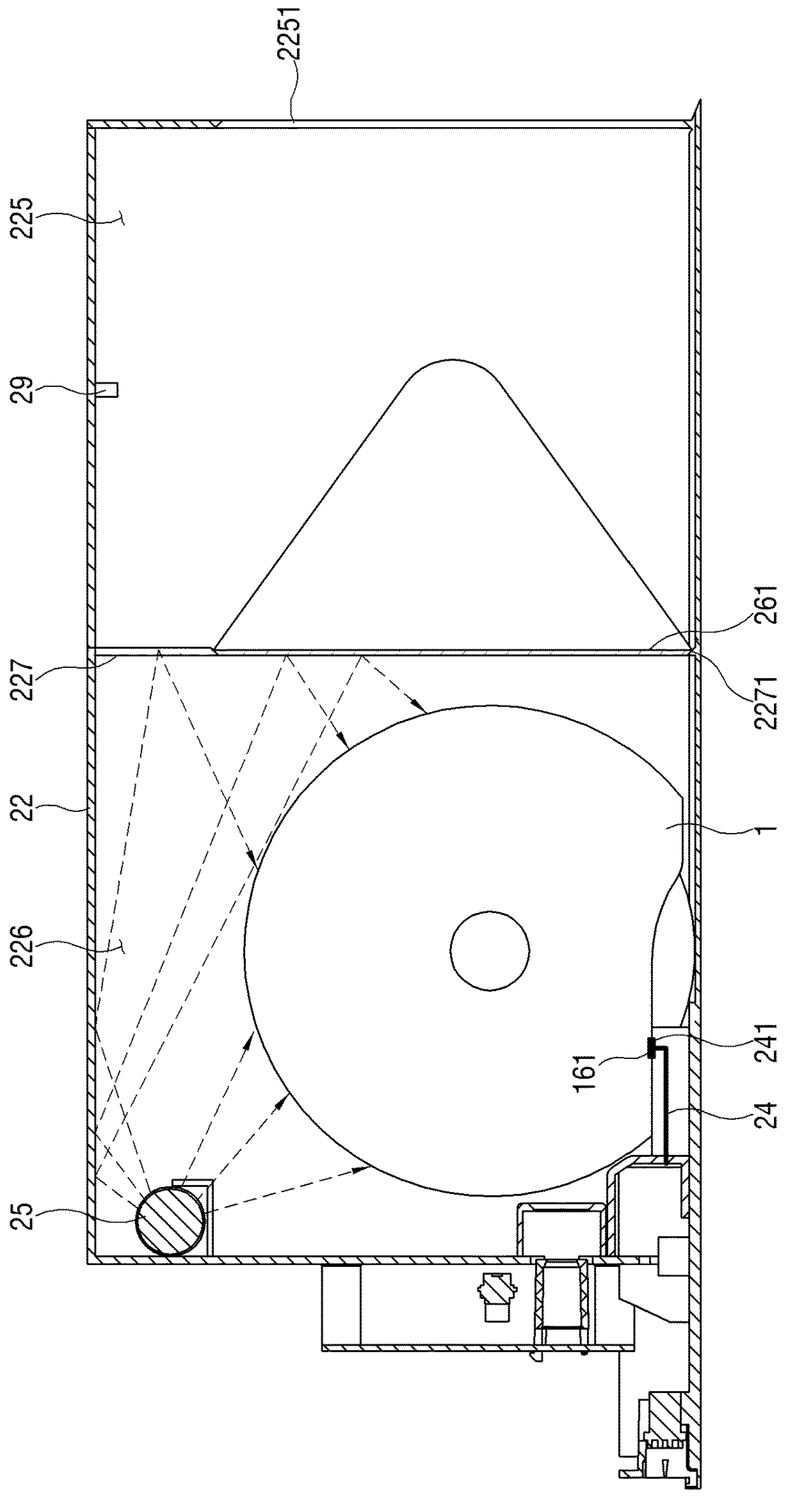
FIG. 15 illustrates that the pet care robot is accommodated in a cleaning space of FIG. 14.
Figure 16:
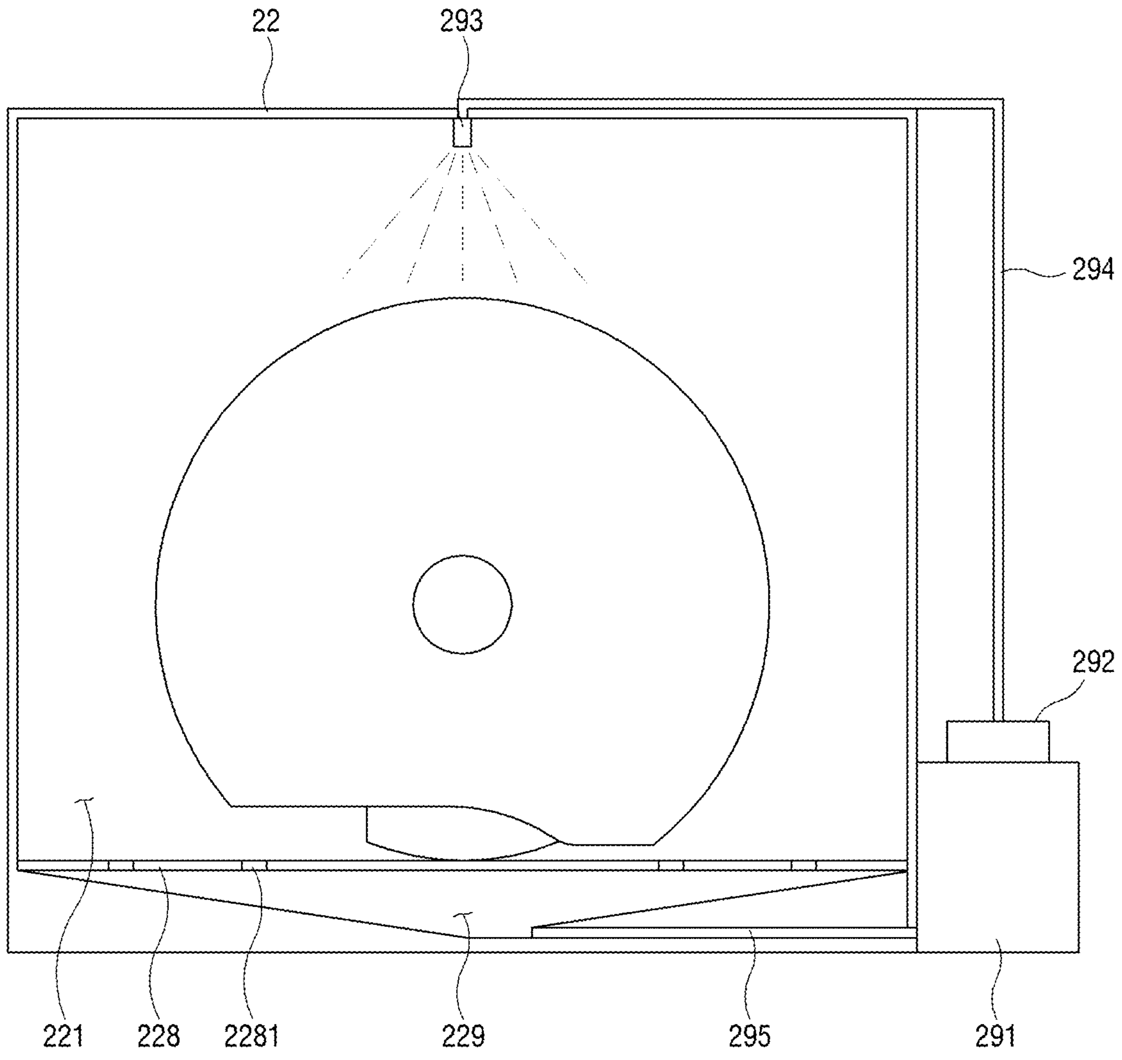
FIG. 16 illustrates that the pet care robot is accommodated in a sterilizing space of FIG. 14.

FIG. 14 illustrates a pet care robot station 2 according to a third embodiment of the disclosure, FIG. 15 illustrates that the pet care robot 1 is accommodated in a cleaning space 225 of FIG. 14, and FIG. 16 illustrates that the pet care robot 1 is accommodated in a sterilizing space 226 of FIG. 14.

Referring to FIG. 14, the inner housing 22 is partitioned into a cleaning space 225 and a sterilizing space 226 by a partition wall 227. The inner housing 22 includes the sterilizer 25, and the cleaning unit 29 provided in the cleaning space 225. The sterilizer 25 and the cleaning unit 29 have structures similar to those described above, and thus repetitive descriptions thereof will be avoided.

The cleaning space 225 includes a front entrance 2251 in the front thereof to allow the pet care robot 1 to come in and out.

The partition wall 227 includes a robot through hole 2271 through which the pet care robot 1 passes between the cleaning space 225 and the sterilizing space 226.

The cleaning space 225 includes the cleaning unit 29 to spray the cleanser. The cleanser may clean foreign materials, for example, germs, viruses, and the like smeared on the outer surface of the pet care robot 1.

The sterilizing space 226 includes the sterilizer 26 to emit the UV light. The UV light may sterilize microorganisms by oxidizing organic materials.

The door 261 is supported at both lateral walls of the cleaning space 225 as shown in FIG. 7 in order to move between a first position for blocking the front entrance 2251 of the cleaning space 225 and a second position for blocking the robot through hole 2271.

In addition, the cleaning space 225 may further include a hot air generator to dry the sprayed cleanser, or a cleaner to clean the sprayed cleanser.

The pet care robot station 2 according to the third embodiment of the disclosure may operate in the cleaning mode and the sterilizing mode.

Referring to FIG. 15, in the cleaning mode, the pet care robot 1 may be guided to the cleaning space 225 when the charging is needed or when foreign materials are detected on the outer surface. When the pet care robot 1 is accommodated in the cleaning space 225, the second processor 28 rotates the door 261 to the first position, thereby blocking the front entrance 2251. Then, the second processor 28 controls the cleaning unit 29 to spray the cleanser to the outer surface of the pet care robot 1.

Referring to FIG. 16, in the sterilizing mode, the pet care robot 1 may be guided to the sterilizing space 226 when the cleaning is completed in the cleaning space 225. When the pet care robot 1 is accommodated in the sterilizing space 226, the second processor 28 rotates the door 261 to the second position to block the robot through hole 2271. Then, the second processor 28 controls the sterilizer 25 to irradiate the outer surface of the pet care robot 1 with the UV light. In this case, the UV light not only removes viruses or germs smeared on the outer surface of the pet care robot 1 but also dries the cleanser used in the cleaning mode. At this time, people or pets are not exposed to the UV light emitted in the sterilizing mode because of the door 261 blocking the robot through hole 2271 and the presence of the cleaning space 225.

The pet care robot station 2 may perform the charging mode after the sterilizing mode or simultaneously with the sterilizing mode.

Figure 17:
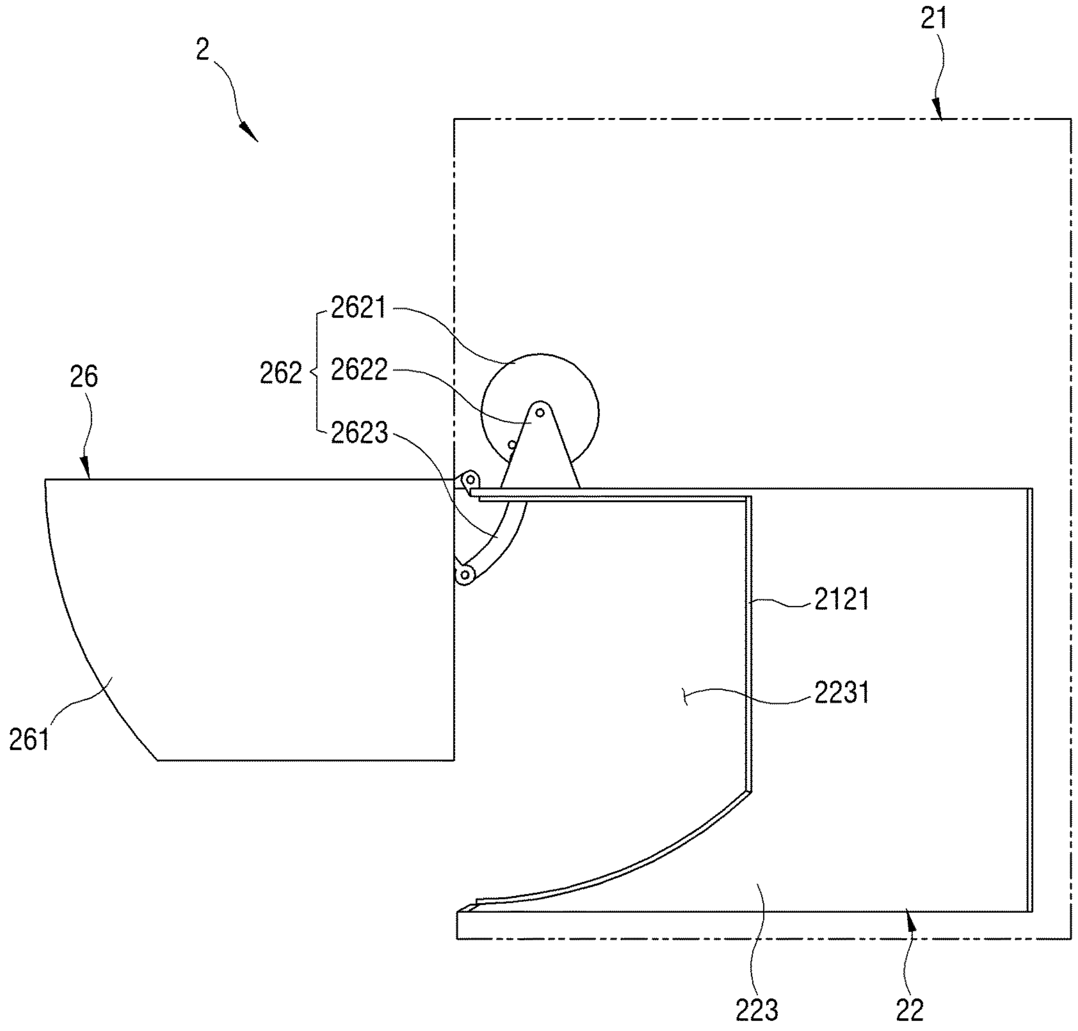
FIG. 17 illustrates a lateral view illustrating a pet care robot station according to a fourth embodiment of the disclosure.
Figure 18:
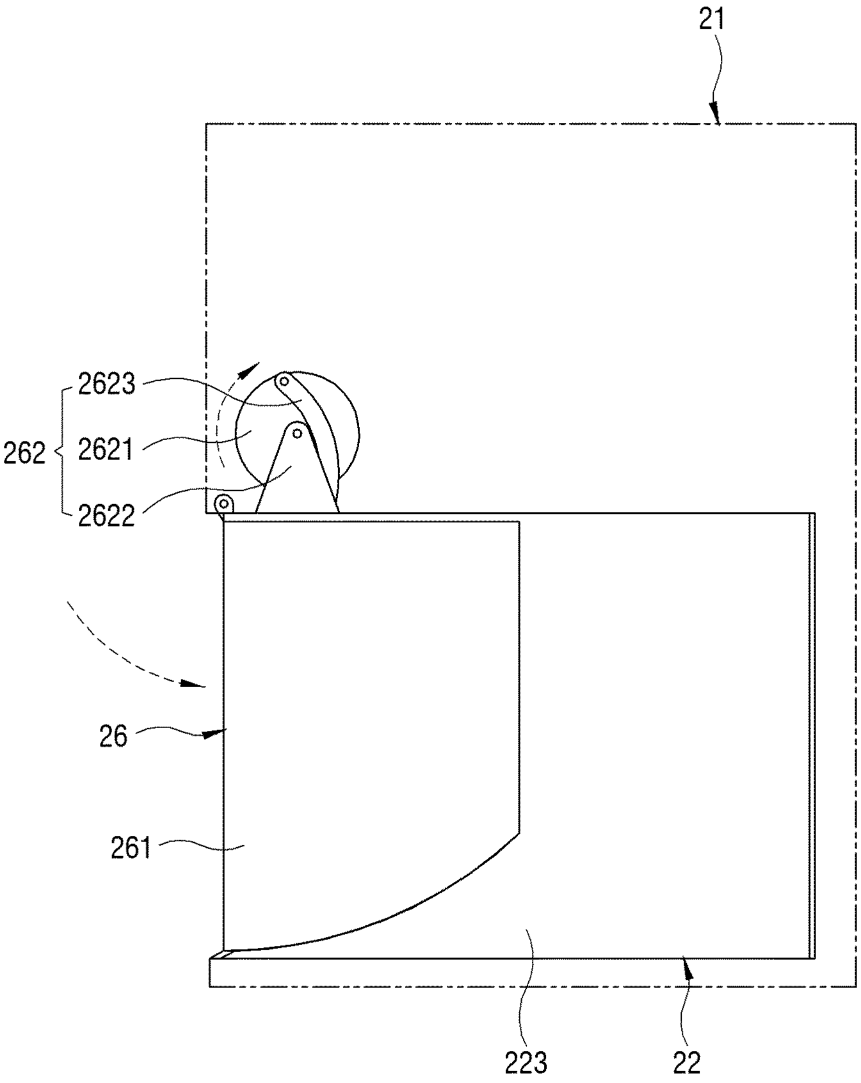
FIG. 18 illustrates that a door is closed in FIG. 17.
Figure 19:
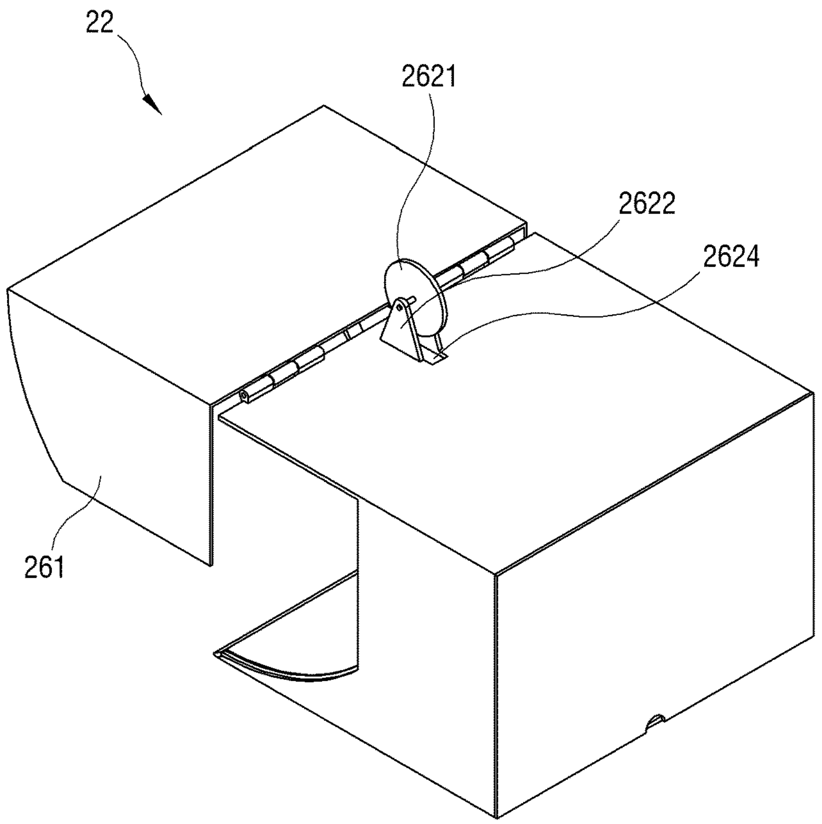
FIG. 19 illustrates an inner housing of FIG. 17.
Figure 20:
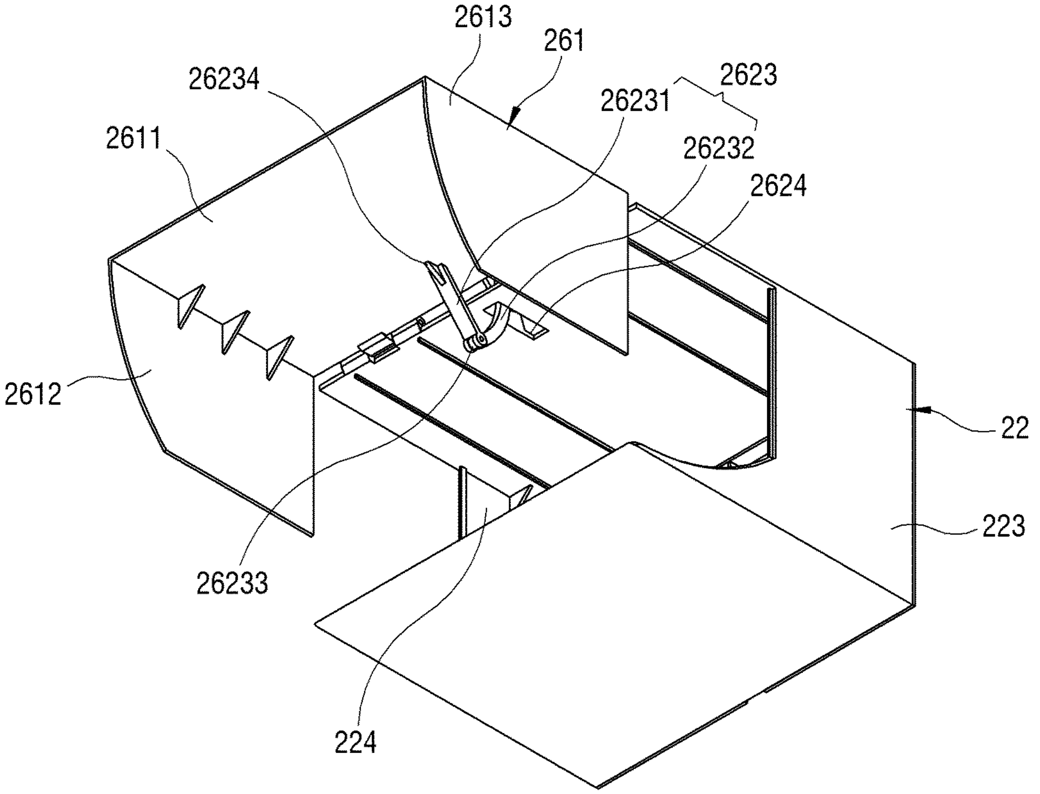
FIG. 20 illustrates an inner housing of FIG. 18.

FIG. 17 is a lateral view illustrating a pet care robot station 2 according to a fourth embodiment of the disclosure, FIG. 18 illustrates that the door 261 is closed in FIG. 17, FIG. 19 illustrates the inner housing 22 of FIG. 17, and FIG. 20 illustrates the inner housing 22 of FIG. 18.

Referring to FIGS. 17 to 20, the pet care robot station 2 includes the outer housing 21, the inner housing 22 accommodated in the outer housing 21, and the door assembly 26.

The outer housing 21 includes the entrance 2121 through which the pet care robot 1 enters and exit. The entrance 2121 is recessed backwards at front and opposite lateral sides.

The inner housing 22 includes opposite lateral sides 223 and 224 (e.g., opposite lateral walls) formed with cutting portions 2231 and 2241 recessed backwards to engage with supporters 2612 and 2613 of the door 261. The opposite lateral sides 223 and 224 are from among the at least one wall that forms the accommodating space. The supporters 2612 and 2613 can be a pair of wing portions of the door 261. The cutting portions 2231 and 2241 allow a signal emitted from the second sensor (e.g., an IR sensor) in the pet care robot station 2 to be transmitted to the outside, thereby preventing a control error of the pet care robot 1.

The door assembly 26 includes the door 261 and the door actuator 262.

The door 261 is rotatably supported on the front of the outer housing 21. The door 261 may open and close the entrance 2121 of the outer housing 21 in the form of a hatchback. The door 261 may include the front blocking plate 2611, and the pair of wing portions 2612 and 2613 bent and extended from the opposite lateral sides of the front blocking plate 2611.

The door actuator 262 may include a wheel 2621 provided on the top of the inner housing 22 and shaped like a disc, a pair of wheel supporters 2622 spaced apart from each other and rotatably supporting the opposite ends of the rotary shaft of the wheel 2621, and a crank 2623 provided between the wheel 2621 and the front blocking plate 2611 of the door 261.

The crank 2623 includes a first crank arm 26231 and a second crank arm 26232. The first crank arm 26231 includes a first end supported on the wheel 2621 after passing through a hole 2624 provided on the top of the inner housing 22, and a second end rotatably coupled to the second crank arm 26232 by a hinge pin 26233. The second crank arm 26232 includes a second end supported on the front blocking plate 2611 of the door 261.

In FIG. 17, when the wheel 2621 of the door actuator 262 is rotated counterclockwise, the first crank arm 26231 of which the first end is supported on the wheel 2621 is rotated together to pull the second crank arm 26232. Therefore, the door 261 supported on the second crank arm 26232 closes the entrance 2121 of the outer housing 21 as shown in FIG. 18.

In FIG. 18, when the wheel 2621 of the door actuator 262 is rotated clockwise, the first crank arm 26231 of which the first end is supported on the wheel 2621 is rotated together to push the second crank arm 26232. Therefore, the door 261 supported on the second crank arm 26232 opens the entrance 2121 of the outer housing 21 as shown in FIG. 17.

In this way, the door 261 is opened and closed in the form of a hatchback, thereby sealing the entrance 2121 of the outer housing 21. Therefore, the UV light for the sterilization is prevented from leakage.

Although exemplary embodiments of the disclosure have been shown and described, the disclosure is not limited to the foregoing specific embodiments, various alternative modifications can be embodied by a person having an ordinary skill in the art without departing from the scope of the disclosure as claimed in the appended claims, and such modified embodiments should not be understood separately from the technical sprit or prospect of the disclosure.

Although the present disclosure has been described with various embodiments, various changes and modifications may be suggested to one skilled in the art. It is intended that the present disclosure encompass such changes and modifications as fall within the scope of the appended claims.

What is claimed is:

1. A pet care robot station comprising:

a housing comprising an entrance configured to allow a pet care robot to enter and exit, and an accommodating space configured to accommodate the pet care robot, wherein the accommodating space comprises a cleaning space including a cleaning unit with which to spray cleanser on an outer surface of the pet care robot, and a sterilizing space partitioned by a partition wall from the cleaning space including an ultraviolet (UV) lamp with which to sterilize the pet care robot via UV light; and a door in the housing and configured to open and close the entrance, wherein the door comprises:

a blocking plate; and a pair of supporters at opposite sides of the blocking plate and rotatably supported on opposite lateral walls of the entrance.

2. The pet care robot station of claim 1, wherein the accommodating space comprises a reflective material on an inner wall of the accommodating space and configured to reflect the UV light.

3. The pet care robot station of claim 1, wherein the door comprises a reflective material on a surface of the door, the surface facing inside of the accommodating space and configured to reflect the UV light.

4. The pet care robot station of claim 1, wherein the blocking plate is larger than the entrance.

5. The pet care robot station of claim 4, wherein the door comprises a motor configured to rotate the pair of supporters.

6. The pet care robot station of claim 1, further comprising a charger in the accommodating space and configured to charge the pet care robot.

7. The pet care robot station of claim 6, further comprising:

a sensor configured to detect a location of the pet care robot; and a processor configured to guide the pet care robot from the detected location to be located in contact with the charger.

8. The pet care robot station of claim 1, wherein the housing comprises a wheel guide on a bottom of the housing, the wheel guide to guide the pet care robot to a charger in the accommodating space.

9. The pet care robot station of claim 1, further comprising:

a sensor configured to detect foreign materials on an outer portion of the pet care robot; and a processor configured to call the pet care robot to the accommodating space based on the foreign materials detected on the outer portion of the pet care robot.

10. The pet care robot station of claim 1, wherein the cleaning unit comprises a cleaning nozzle configured to spray the cleanser onto a surface of the pet care robot.

11. The pet care robot station of claim 1, wherein the cleaning space comprises a front entrance configured to allow the pet care robot to enter and exit the cleaning space, and the door is configured to selectively rotate between a first position for blocking the front entrance and a second position for blocking the robot through hole.

12. The pet care robot station of claim 1, wherein the pair of supporters is extended in a backwards direction from a front of the blocking plate.

13. The pet care robot station of claim 1, wherein the entrance is opened toward in a forward direction of the housing.

14. An inner housing of a pet care robot station, the inner housing comprising:

at least one wall in a shape of a box that forms an accommodating space, the box including an opening through which a pet care robot can enter and exit the accommodating space;

the accommodating space configured to accommodate the pet care robot, wherein the accommodating space comprises a cleaning space including a cleaning unit with which to spray cleanser on an outer surface of the pet care robot, and a sterilizing space partitioned by a partition wall from the cleaning space including an ultraviolet (UV) lamp with which to sterilize the pet care robot via UV light; and a door in the housing and configured to open and close the opening, wherein the door comprises:

a blocking plate; and a pair of supporters at opposite sides of the blocking plate and rotatably supported on opposite lateral walls of the opening.

15. The inner housing of claim 14, wherein the pair of supporters is extended in a backwards direction from a front of the blocking plate.

16. The inner housing of claim 14, wherein the opening is opened toward in a forward direction of the housing.

* * * * *